United States Patent
Ross et al.

(10) Patent No.: US 7,141,068 B2
(45) Date of Patent: Nov. 28, 2006

(54) SPINAL SPACER ASSEMBLY

(76) Inventors: Thomas Ross, 9800 Metric Blvd., Austin, TX (US) 78758; Wayne P. Gray, 9800 Metric Blvd., Austin, TX (US) 78758

( * ) Notice: Subject to any disclaimer, the term of this patent is extended or adjusted under 35 U.S.C. 154(b) by 465 days.

(21) Appl. No.: 10/609,679

(22) Filed: Jul. 1, 2003

(65) Prior Publication Data
US 2005/0004671 A1 Jan. 6, 2005

(51) Int. Cl.
A61F 2/44 (2006.01)

(52) U.S. Cl. .................................. 623/17.11

(58) Field of Classification Search ............ 623/11.11, 623/16.11, 18.11, 17.11–17.16
See application file for complete search history.

(56) References Cited

U.S. PATENT DOCUMENTS

| | | | | |
|---|---|---|---|---|
| 4,961,740 | A | * | 10/1990 | Ray et al. ................... 606/61 |
| 5,458,638 | A | * | 10/1995 | Kuslich et al. ........... 623/17.11 |
| 5,609,637 | A | | 3/1997 | Biedermann et al. |
| 5,702,451 | A | | 12/1997 | Biedermann et al. |
| 5,860,973 | A | * | 1/1999 | Michelson ................... 606/61 |
| 5,904,719 | A | * | 5/1999 | Errico et al. .............. 623/17.16 |
| 5,972,031 | A | | 10/1999 | Biedermann et al. |
| 6,086,613 | A | * | 7/2000 | Camino et al. ........... 623/17.16 |
| 6,136,031 | A | * | 10/2000 | Middleton ................ 623/17.16 |
| 6,375,681 | B1 | | 4/2002 | Truscott |
| D463,560 | S | | 9/2002 | Michelson |
| 6,824,565 | B1 | * | 11/2004 | Muhanna et al. ......... 623/17.16 |
| 6,899,734 | B1 | * | 5/2005 | Castro et al. ............ 623/17.16 |
| 2003/0028197 | A1 | * | 2/2003 | Hanson et al. ................. 606/99 |
| 2003/0139812 | A1 | * | 7/2003 | Garcia et al. ............ 623/17.11 |

OTHER PUBLICATIONS

Mellion, Dr. B. Theo.—NeckReference.com—Treatment Options—Access: <http://www.neckreference.com/treatment-surgical-corpectomy.html>.

* cited by examiner

*Primary Examiner*—Eduardo C. Robert
*Assistant Examiner*—Anu Ramana
(74) *Attorney, Agent, or Firm*—Chambliss, Bahner & Stophel, P.C

(57) ABSTRACT

A spinal spacer assembly comprises spacer tubes of different cross sections including kidney shaped, oblong, oval and round. The spacer tubes have internal ribs for receiving top and bottom end caps. Such end caps are pressed into the top and bottom openings of the spacer tube so as to be supported on and frictionally engage the internal ribs. The end caps are flush with the tops and bottoms of the spacer tubes except for serrations on the end caps which may project outwardly therefrom.

2 Claims, 24 Drawing Sheets

SPINAL SPACER ASSEMBLY

FIELD OF THE INVENTION

This invention relates to spinal spacer assemblies for insertion into an intervertebral space and/or for replacement of a portion of a vertebrae.

BACKGROUND OF THE INVENTION

The present invention relates to spinal spacer assemblies for use in spinal fusion procedures. Spinal fusion employs the use of spacer assemblies comprising a hollow mesh spacer tube and end caps, which assemblies act to space apart and fuse together adjacent vertebrae. These mesh spacer tubes are often formed of titanium and are available in varying shapes and sizes. In addition, they can be trimmed on site by the surgeon to provide a better individual fit for each patient.

Spinal spacer assemblies of this type are shown in a number of U.S. patents including Biedermann et al U.S. Pat. No. 5,702,451, Biedermann et al U.S. Pat. No. 5,972,031, Camino et al U.S. Pat. No. 6,086,613 and the Truscott U.S. Pat. No. 6,375,681. These patents show a number of known spinal spacer assemblies comprising a hollow mesh spacer tube which can be trimmed to different heights and having upper and lower end caps. These patents also illustrate that spinal spacer assemblies of the present type are provided in different cross sections. Such spacer assemblies are generally hollow and include openings in the side thereof to provide access for bone to grow and fuse within the mesh tube.

The need exists for further improvements in the field of spinal spacer assemblies of the present type.

SUMMARY OF THE INVENTION

Thus, an object of the present invention is to provide improvements in the field of spinal spacer assemblies and the components thereof.

According to one aspect of the present invention, spacer tubes are provided in varying heights and different cross sections all having in common a structure for receiving a pair of end caps which can be friction fit entirely within the space defined by planes passing through the interior surfaces of the spacer tube. The spacer tubes include ribs on the internal walls thereof for supporting the end caps which are pushed into the upper and lower ends of the spacer tube. The end caps include friction elements which frictionally engage at least one supporting structure of the spacer tube. The spacer tube along with its two end caps comprise a spinal spacer assembly.

In accordance with another aspect of the present invention, the outwardly facing upper and lower faces of the end caps may include serrations for increasing the surface area of engagement and thus effecting a better engagement with the surfaces of the vertebrae which they face. The serrations may have smooth rounded crests, which are suitable for insertion of the spacer assembly either anteriorly or posteriorly. Alternatively, the serrations may be formed with sharp crests. The sharp crests may be formed asymmetrically. While the spacer assemblies with sharp serrations can also be inserted both anteriorly or posteriorly, some surgeons might prefer to insert these anteriorly to avoid having the sharp serrations from coming close to nerve roots which are in the vicinity of a posterior approach.

The spacer assembly may be constructed in a number of different cross-sectional shapes including kidney shaped, oblong, circular or oval. Any of these shapes may be inserted anteriorly or posteriorly.

The spacer tubes include support structures in the form of vertical ribs on the interior thereof to support the end caps. Placing essentially all of the load on the ribs frees up a substantial portion of the remaining side surface of the spacer tube to allow larger openings to provide better access for bone to grow and fuse within the spacer assembly.

The end caps, after being fully inserted into their respective ends of the spacer tube will be generally flush with that end surface of the spacer tube except for the serrations which extend outwardly beyond that end surface. The serrations may rise to a uniform height or the serrations at one end may rise to a greater height than at the other end, thereby permitting the two adjacent vertebrae to tilt relative to each other to create a lordosis or kyphosis angle.

For use as a fusion spacer assembly in an intervertebral space, one would of course choose a spacer tube of the correct height which might be between 7 and 15 mm. For intervertebral fusion, spacer tubes of all shapes would preferably be formed as a set of different heights, for example 7, 8, 9, 10, 11, 12, 13, 14 and 15 mm, although slight trimming at the ends of the spacer tubes can occur.

In addition to fusion of adjacent vertebrae, the spacer assembly of the present invention can be used in a corpectomy which comprises removal of a portion of a vertebrae and the adjacent intervertebral discs and replacement thereof with a spacer assembly of the present invention which fills the space left in the vertebrae and continues through the two adjacent intervertebral spaces to engage the next upper and lower vertebrae. Corpectomy can also be utilized for two or more adjacent vertebrae, wherein the spacer assembly would be placed in a cavity made in both of the adjacent vertebrae, the intervertebral disc therebetween and in the two intervertebral discs above and below the two vertebrae which have been cut in the course of the corpectomy. For this procedure, one would utilize a circular or oval spacer assembly. For use in corpectomy, the circular or oval spacer tube would be initially provided of a relatively large height, for example up to 130 mm, whereby the surgeon at the site, if requiring a shorter spacer tube for a particular corpectomy procedure, would simply cut the tube to a shorter height.

Thus, an aspect of the present invention is the provision of a system of spacer assemblies of different cross-sectional shapes and heights, and thus adaptable for a large variety of different applications, all having common features of the spacer assembly as described above relating to the arrangement for securing the end caps and other common characteristics.

Thus, it is an object of the present invention to provide a new spinal spacer tube.

It is another object of the present invention to provide a new spinal spacer assembly.

It is another object of the present invention to provide a new system of spinal spacer assemblies.

These and other objects of the present invention will be apparent from the detailed description to follow, together with the accompanying drawings.

BRIEF DESCRIPTION OF THE DRAWINGS

The invention will now be described in detail with respect to preferred embodiments with reference to the accompanying drawings, wherein.

DETAILED DESCRIPTION OF THE PREFERRED EMBODIMENTS

Referring now to the figures, like elements are represented by like numerals throughout the several views.

Figure 1:
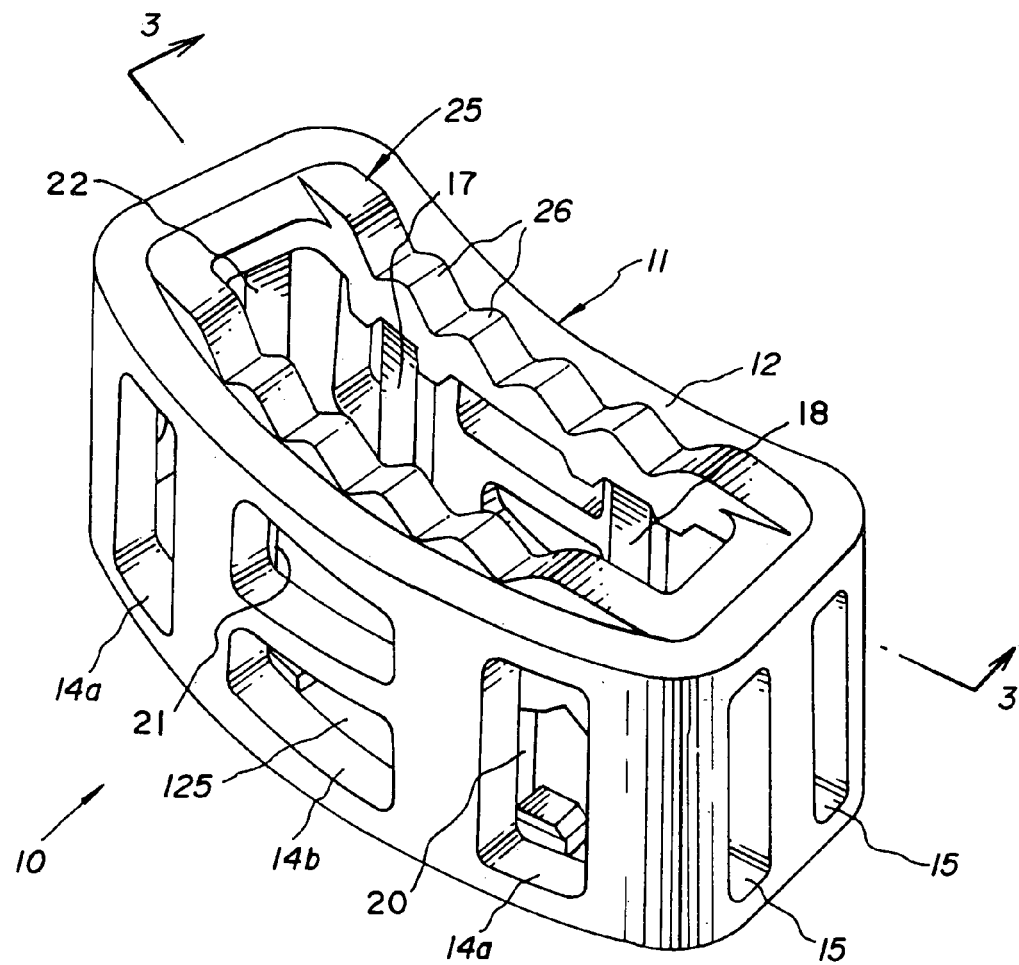
FIG. 1 is a top perspective view of a first embodiment of a spinal spacer assembly which has a kidney shape.
Figure 2:
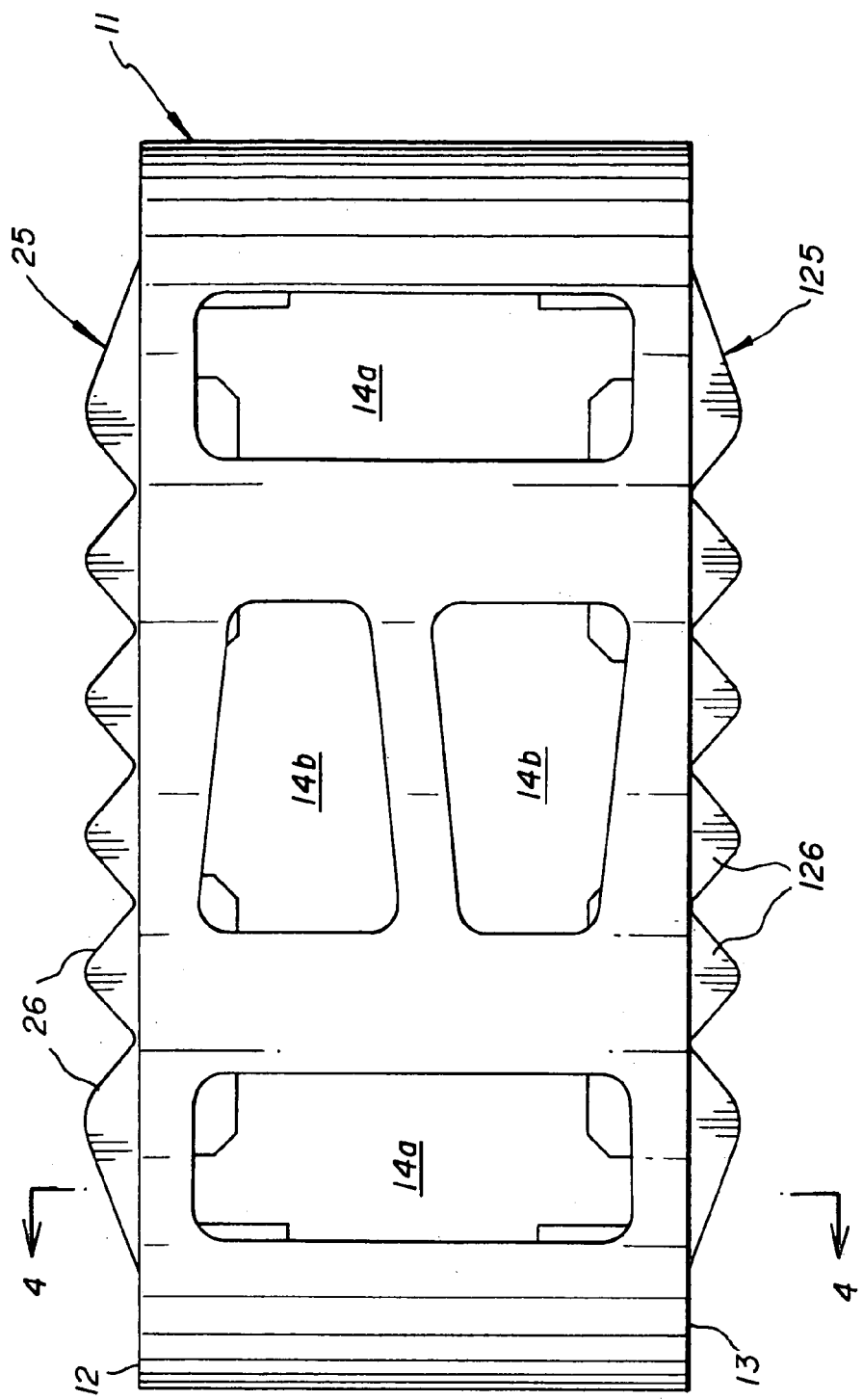
FIG. 2 is a side elevational view of FIG. 1.
Figure 3:
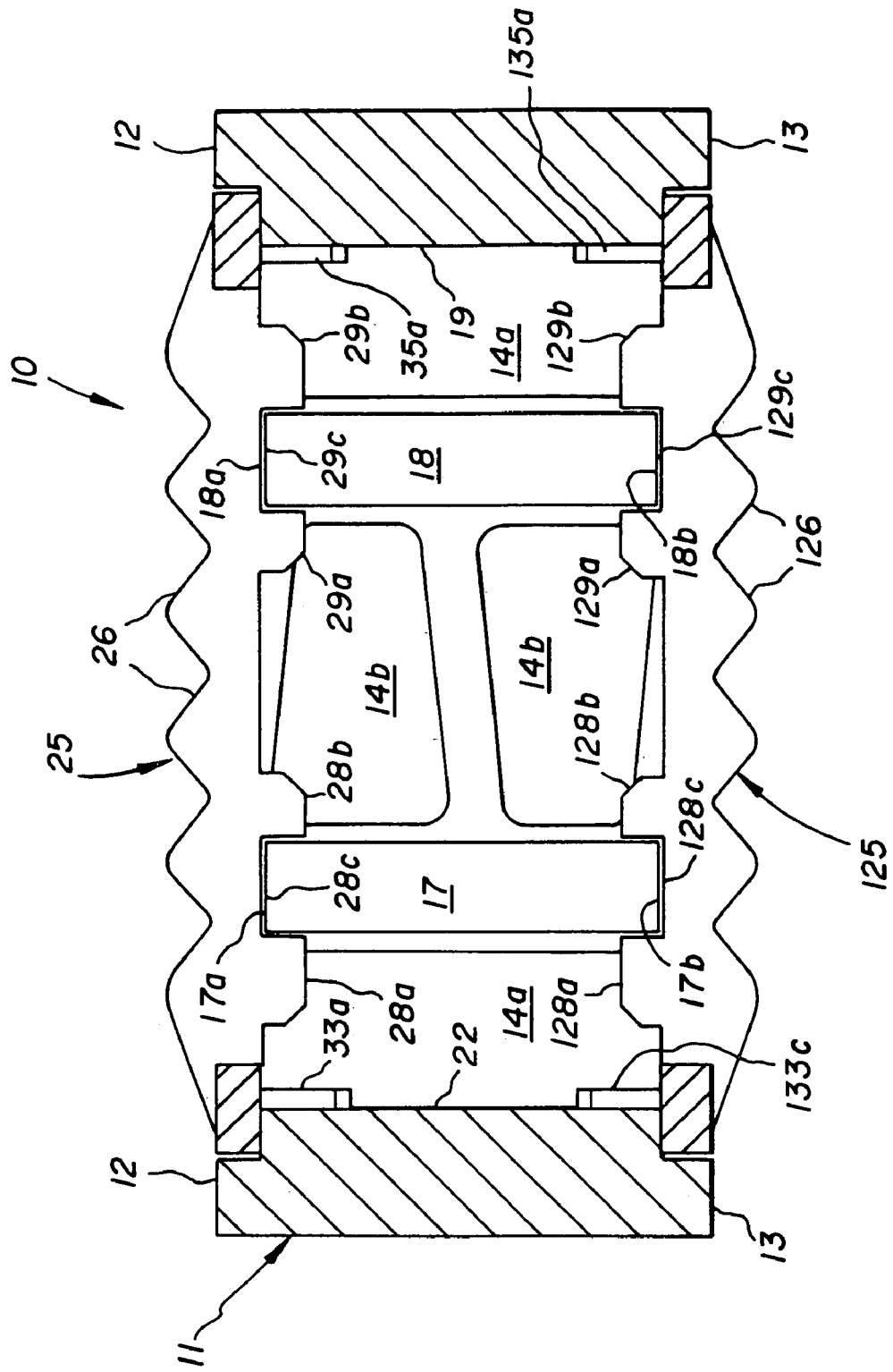
FIG. 3 is a sectional view taken along line 3—3 of FIG. 1.
Figure 4:
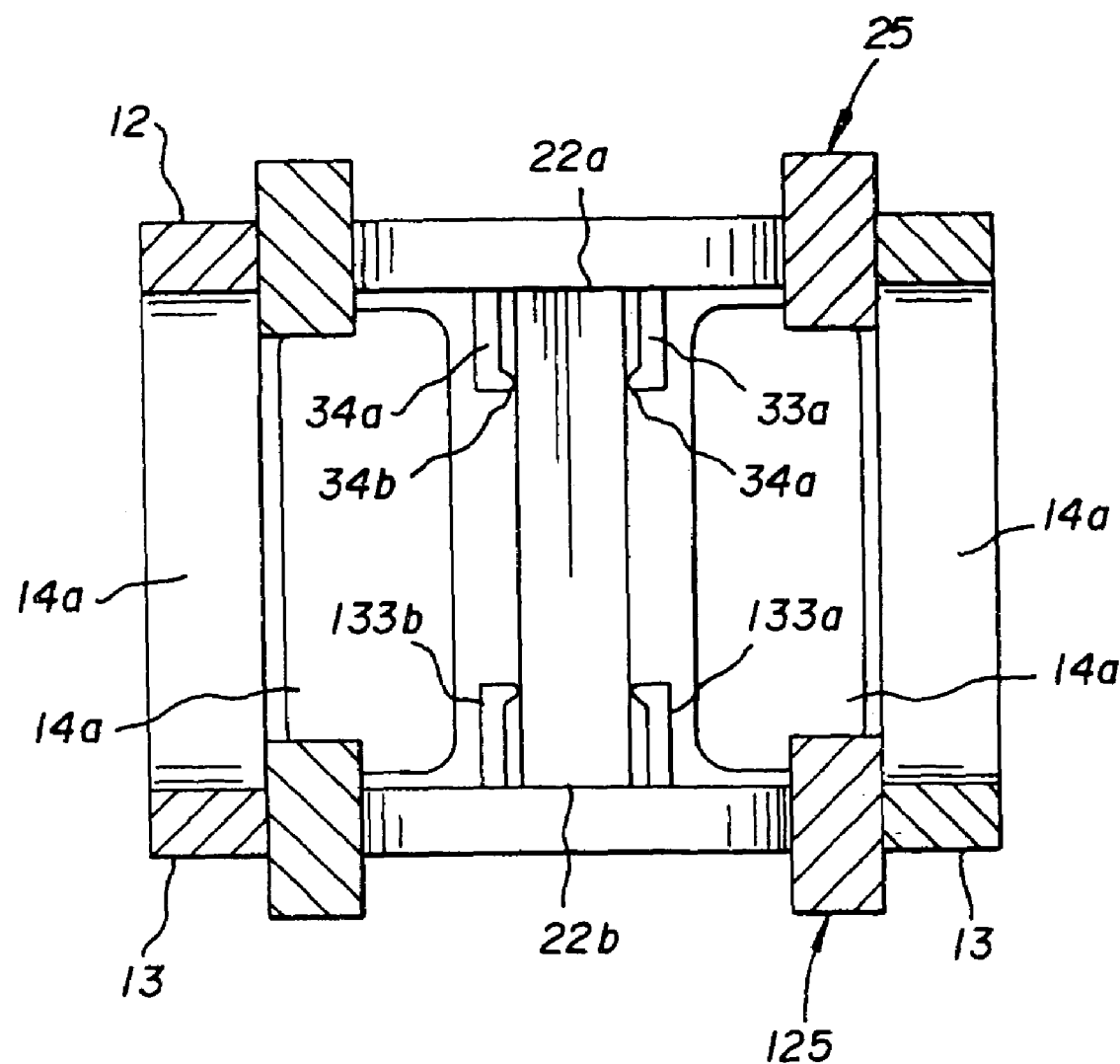
FIG. 4 is a cross-sectional view taken along line 4—4 of FIG. 2.
Figure 5:
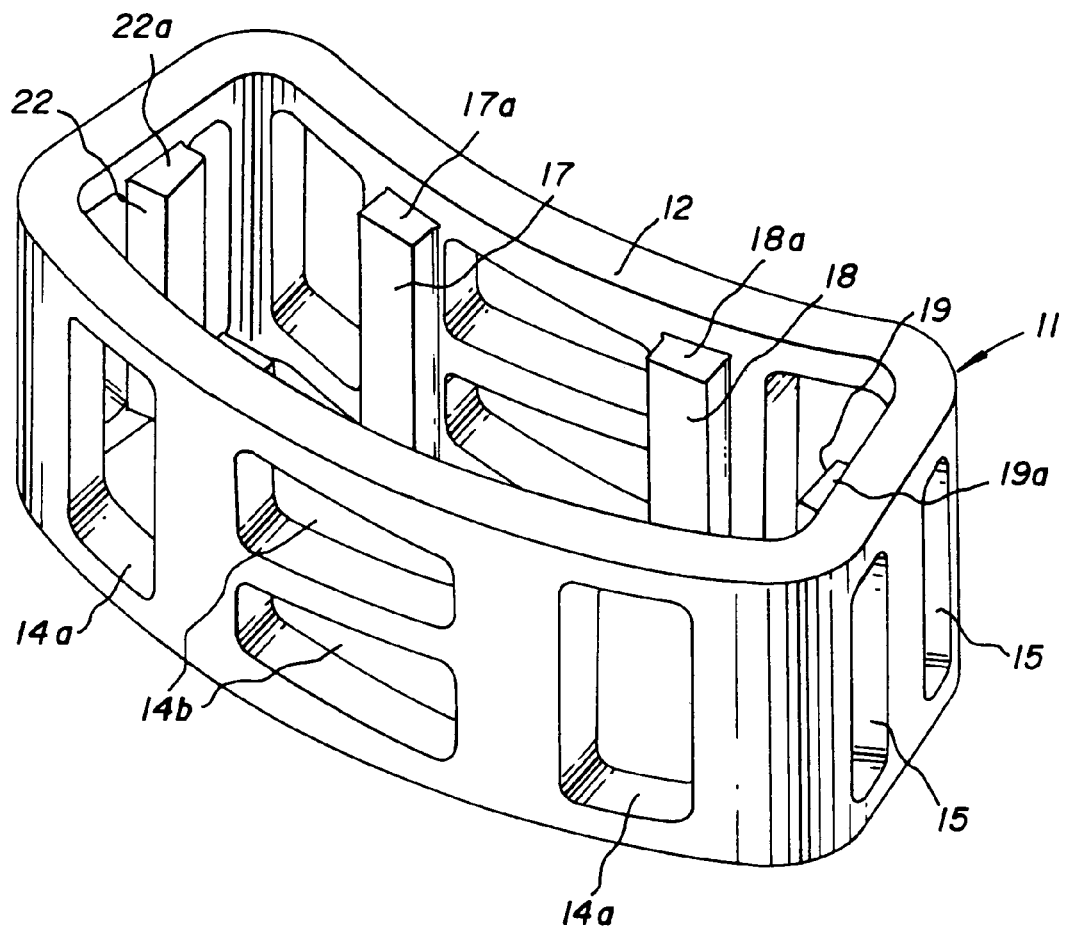
FIG. 5 is a top perspective view of the spacer tube shown in FIGS. 1–4.
Figure 6:
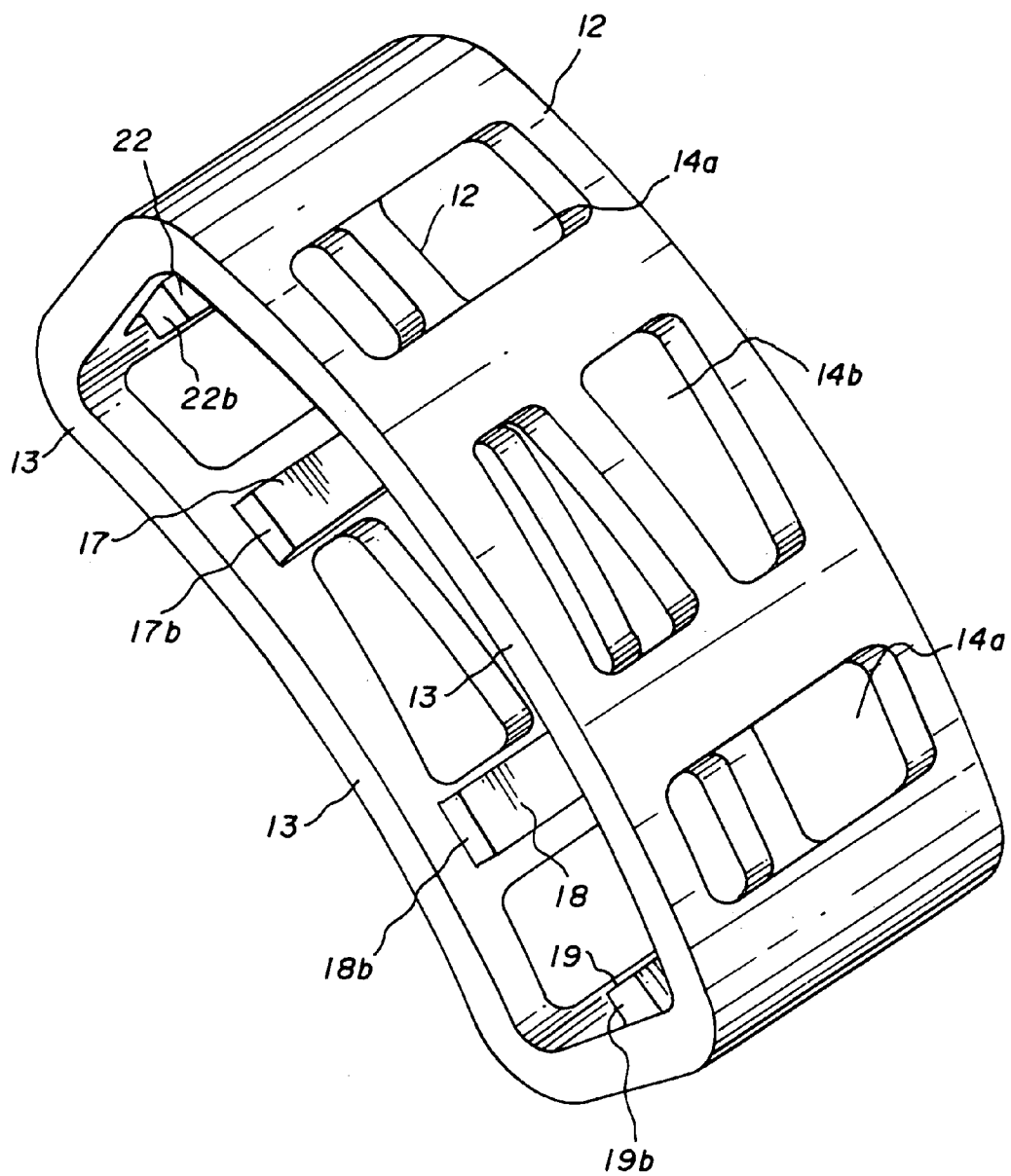
FIG. 6 is a bottom perspective view of the spacer tube shown in FIGS. 1–4.
Figure 7:
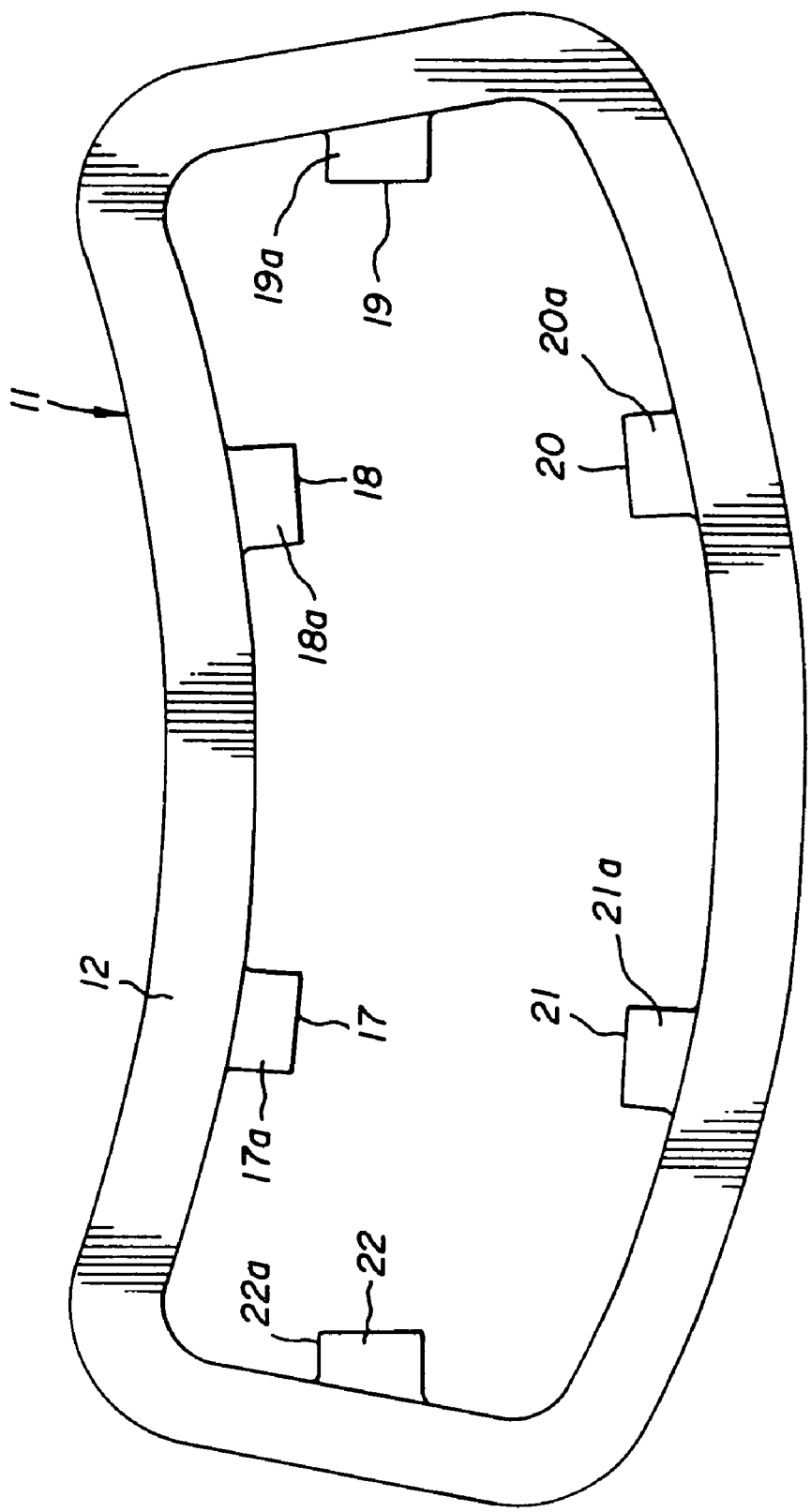
FIG. 7 is a top plan view of the spacer tube shown in FIGS. 1–6.
Figure 8:
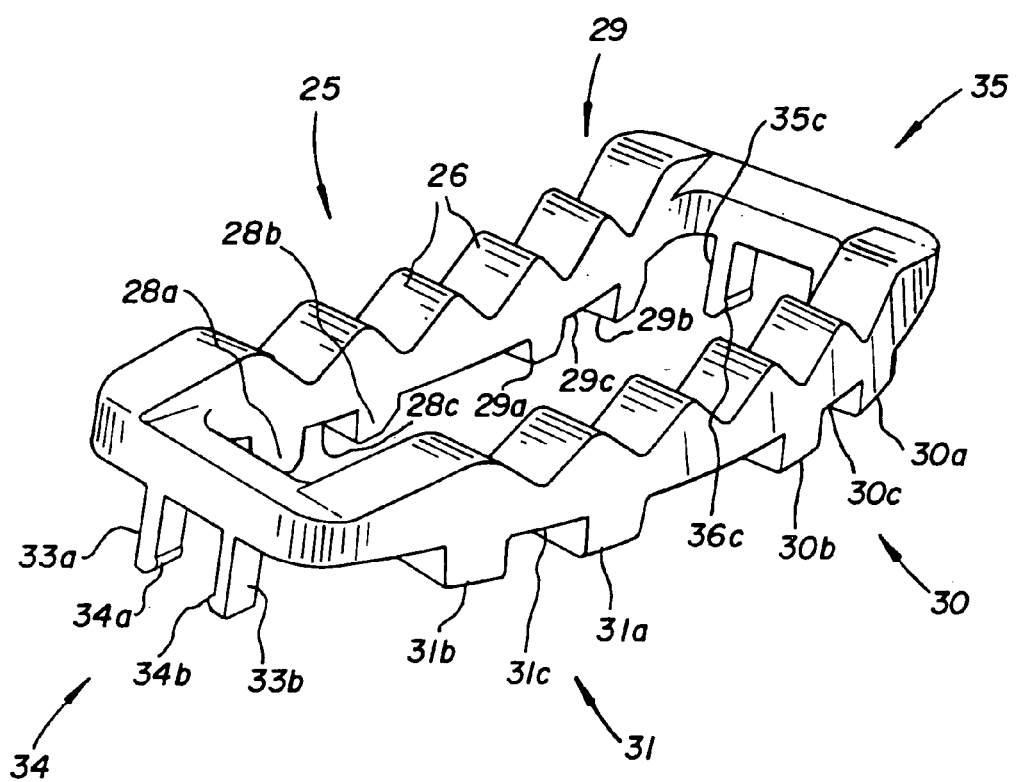
FIG. 8 is a top perspective view of the top end cap shown in FIGS. 1 and 2.
Figure 9:
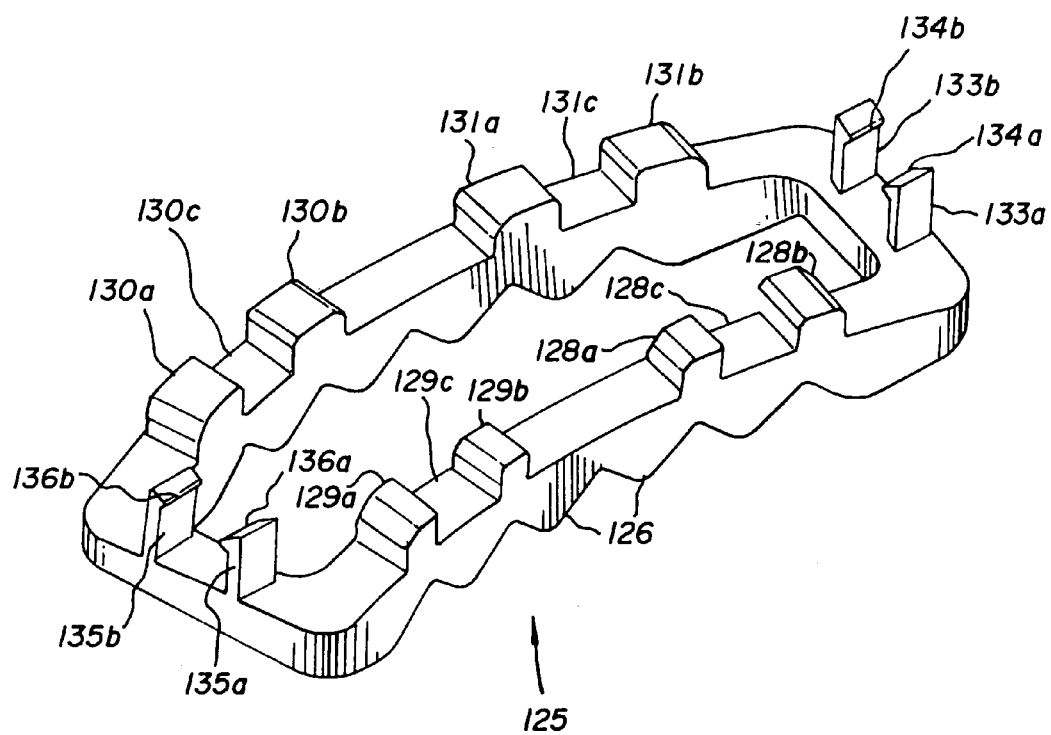
FIG. 9 is a top plan view of the end cap shown in FIGS. 1 and 2.

FIGS. 1–9 illustrate different views of a first embodiment of a spinal spacer assembly according to the present invention, wherein FIGS. 1–4 illustrate the entire assembly, FIGS. 5–7 illustrate the spacer tube 11 and FIGS. 8 and 9 illustrate the end caps.

The spacer tube assembly shown in FIGS. 1–9 is kidney shaped, meaning that it is generally kidney shaped when viewed from above. Referring to FIGS. 1–4, the spacer assembly comprises a spacer tube 11 having a top end cap 25 pressed into the top opening surrounded by the top surface 12 and a lower end cap 125 which is press fit into the bottom opening surrounding the bottom surface 13.

A feature of all embodiments of the present invention is that the upper and lower end caps are inserted through the upper and lower openings, respectively, and are supported by and frictionally engage supporting structures located solely within the interior of the spacer tube and thus not requiring engagement of the end caps with the top and bottom surfaces of the spacer tube. Another feature shown in the embodiment of FIGS. 1–9 but common to all embodiments is that the location of the supporting structures within the interior of the spacer tube permits the formation of relatively large openings in the side wall of the spacer tube to enhance access for bone to grow and fuse within the spacer assembly. Other features common to all of the described embodiments and equivalents thereof will be apparent from the detailed description of the preferred embodiments to follow.

Referring to FIGS. 4–7, the spacer tube 11 comprises a support structure in the form of a plurality of vertically extending ribs 17, 18, 19, 20, 21 and 22 on the interior thereof. The subscript "a" for each denotes the top of each rib and the subscript "b" denotes the bottom of each rib.

FIG. 8 illustrates the top end cap 25. The end cap includes a plurality of pairs of support posts which are indicated generally by the numerals 28, 29, 30 and 31. Each pair of support posts includes a space therebetween. Each of these pairs of support posts are placed down about one of the ribs 17–22. The support posts engage the sides of the ribs rather loosely, essentially to stabilize the same, while the horizontal space between the posts of the pair will be in load bearing relationship to the top of its respective rib. Also shown in FIG. 8 are pairs of friction prongs 34 and 35. Each of these pairs comprise opposing prongs which frictionally engage the side of one of the ribs 17–22 while the horizontal undersurface of the cap between the two friction prongs is not intended to be load bearing against the top of its respective rib. It is to be understood that in the embodiment shown in FIGS. 1–9 as well as all of the other embodiments, there is no specific requirement for a certain number of pairs of support posts or a certain number of pairs of friction prongs, provided that each embodiment has at least one of these at any location, with the other type being provided for other ribs. One particular arrangement suitable for the embodiment of FIGS. 1–9, by way of illustration and not by way of limitation, is shown in FIG. 8. This end cap includes a pair of posts and a flat surface therebetween corresponding to each of the ribs 17, 18, 20 and 21. Referring to FIG. 8 and also to FIG. 3, the end cap 25 includes posts 28a and 28b which straddle the top of the post 17 whereat the flat surface 28c rests upon the top 17a of the rib 17. FIG. 3 also illustrates a similar arrangement for posts 29a and 29b and flat surface 29c with respect to rib 18 and its upper surface 18a. Identical structures are also provided on the opposite side of the top end cap 25 wherein elements 30a–30c cooperate with rib 20 and elements 31a–31c cooperate in identical fashion with rib 21. These pairs of support posts are provided simply to provide a snug fit of the end cap on the respective ribs, to stabilize the end cap, and are not intended to be a tight friction fit.

To securely hold the top end cap 25 within the spacer tube 11, at least one of the ribs of the spacer tube will be frictionally engaged by a pair of prongs which grasp the side of one of the ribs. Friction prongs can be provided on any one or more of the ribs 17–22.

In the embodiment shown in FIGS. 1–9, friction prongs are provided at the ends of the end cap 25 for engagement with the ribs 19 and 22.

Referring to FIGS. 4 and 8, the end cap 25 comprises a pair of friction prongs 33a and 33b which include at the lower ends thereof a pair of inwardly extending friction engaging projections 34a and 34b. At the upper end, the friction prongs 33a and 33b are spaced apart a distance slightly greater than the width of the rib 22, for example approximately 2/1000 inch. Because of this slightly larger spacing, the friction prongs 33a and 33b, will be able to turn inwardly just slightly so that the projections 34a and 34b can frictionally engage the sides of rib 22.

In the embodiment of FIGS. 1–9, friction prongs 35a and 35b are provided at the opposite end of the spacer assembly with projections 36a and 36b to frictionally engage the rib 19 in precisely the same manner as described above with respect to rib 22.

The upper end cap 25 is designed such that when the support posts engage their respective ribs, the upper end cap is essentially flush with the top surface 12 of the spacer assembly 10 except for serrations 26 which extend above the surface 12, particularly along the lateral surfaces thereof. The serrations 26 enhance engagement of the spacer assembly with the adjacent vertebral surface.

FIG. 9 illustrates the bottom end cap 125. As noted above, there is wide latitude in deciding which of the ribs will receive support posts and which will receive friction prongs. Whatever is selected for the top end cap, the bottom end cap would be a mirror image thereof. Thus, the bottom end cap shown in FIG. 9 is a mirror image of the upper end cap 25. Accordingly, for convenience all elements of the bottom end cap 25 have the same numerals as for the top end cap 25 except raised by 100. Also, the engagement of the support posts and friction prongs with the bottoms of the ribs 17–22 would be identical to the manner as described above with respect to the top end cap 25. Such identical engagement can be seen for example in FIGS. 3 and 4. Accordingly, the identical engagement of the bottom end cap with the spacer tube 10 will not be further discussed in detail.

As noted above, the location of the supporting structure leaves room for relatively large openings through the side wall of the spacer tube. As shown in FIGS. 1–6, the openings 14 take the form of long vertically elongated rectangles 14a and horizontally elongated irregular trapezoids 14b.

Figure 10:
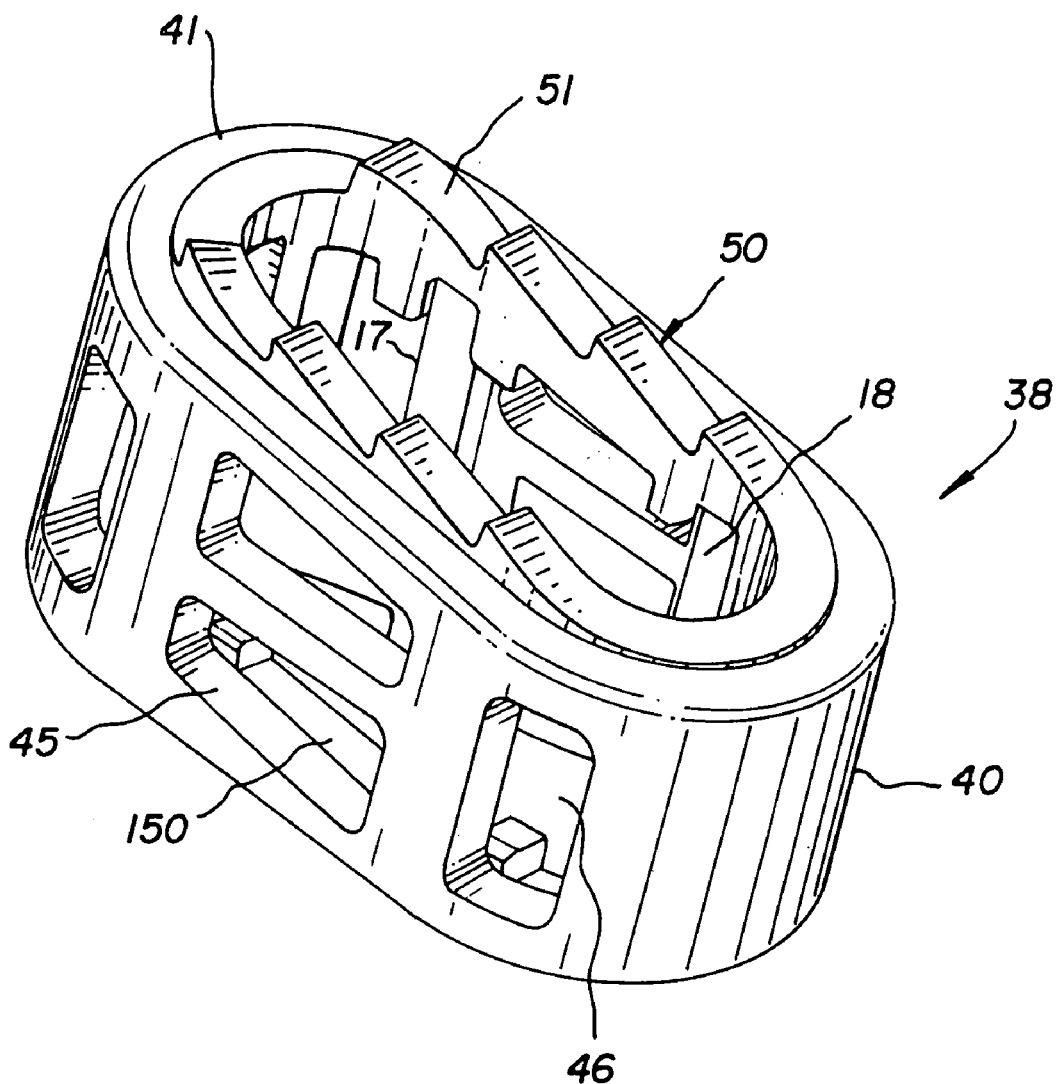
FIG. 10 is a top perspective view of another embodiment of a spinal spacer assembly which has an oblong shape.
Figure 11:
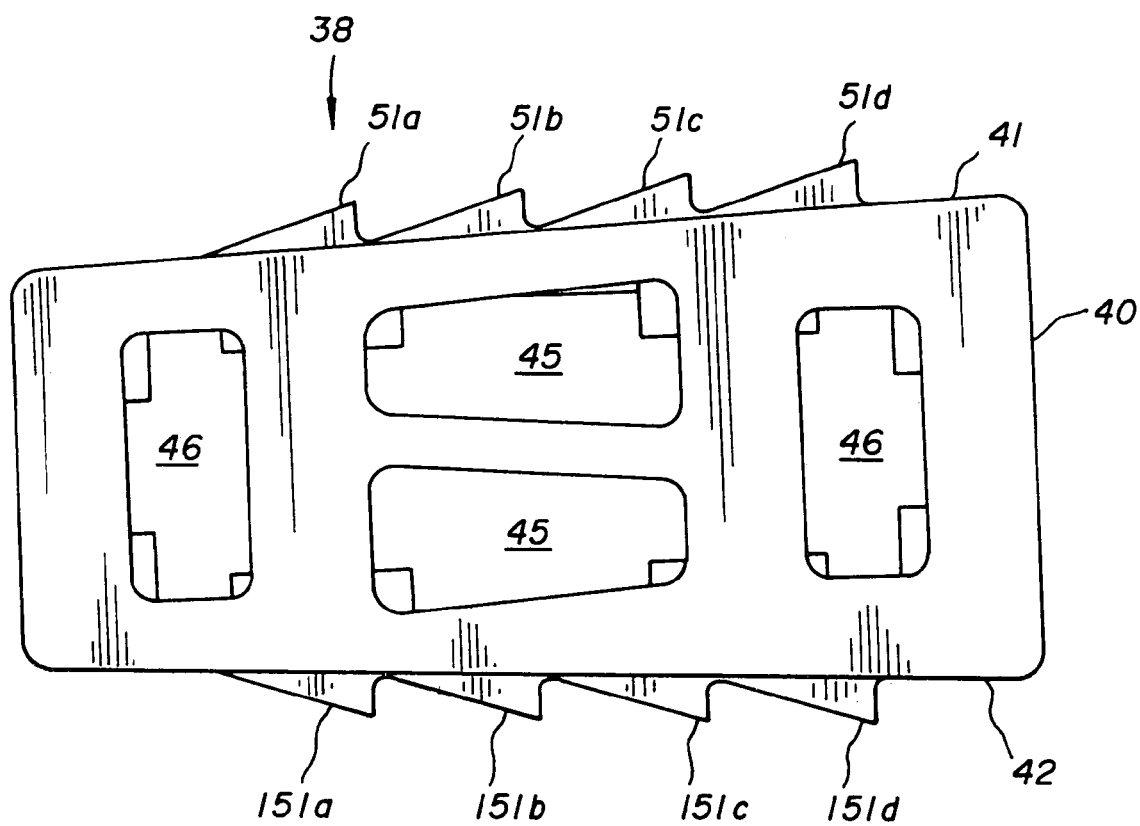
FIG. 11 is a side elevation view of the spacer assembly of FIG. 10.

FIGS. 10–17 illustrate another embodiment of the invention. FIGS. 10 and 11 illustrate another embodiment 38 of a spacer assembly which is oblong in shape which is best seen by comparing the plan view of FIG. 14 with the plan view of FIG. 7. Spacer assembly 38 comprises an oblong spacer tube 40 having a top surface 41 and a bottom surface 42.

Figure 12:
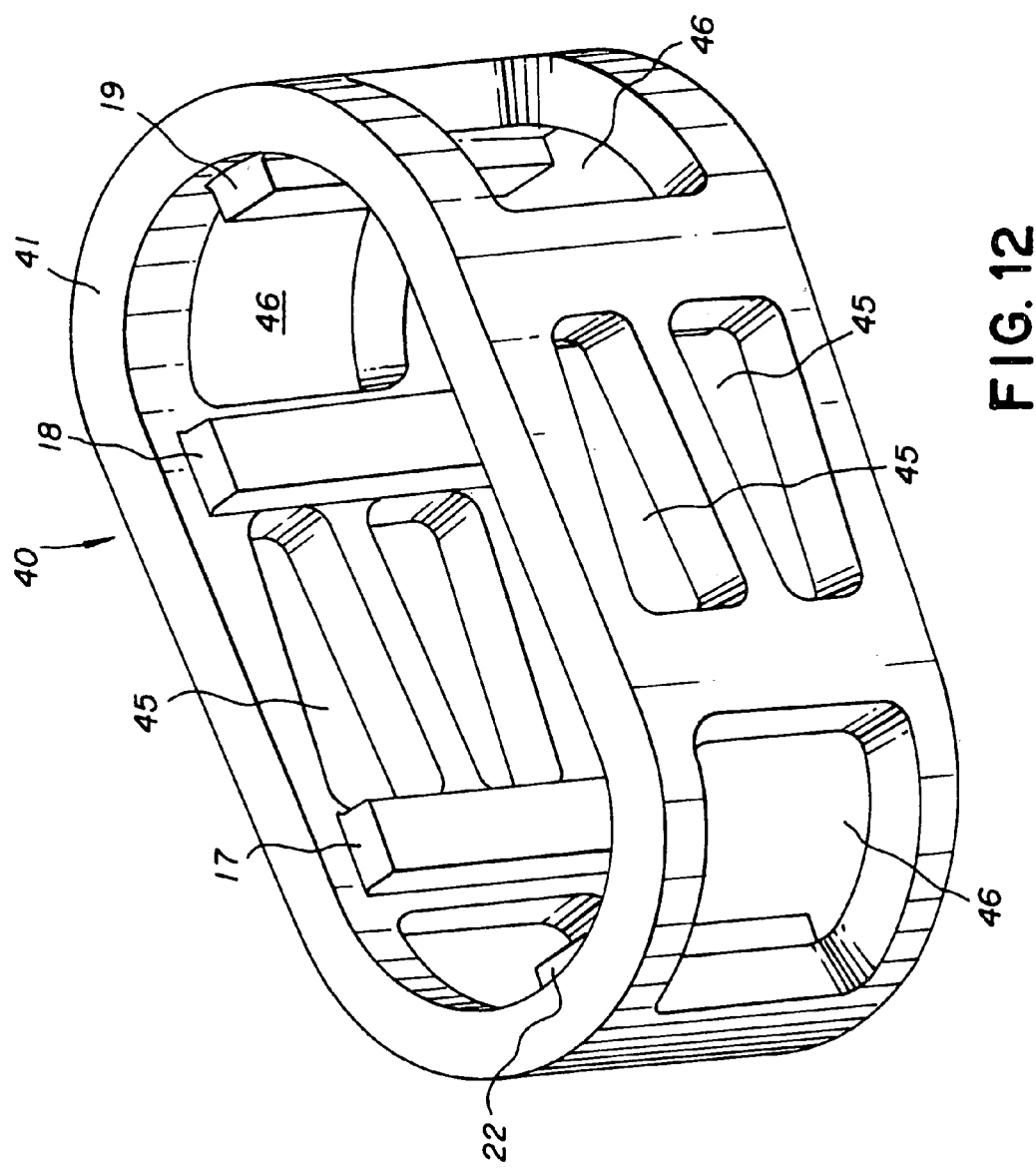
FIG. 12 is a top perspective view of the spacer tube of FIGS. 10 and 11.
Figure 13:
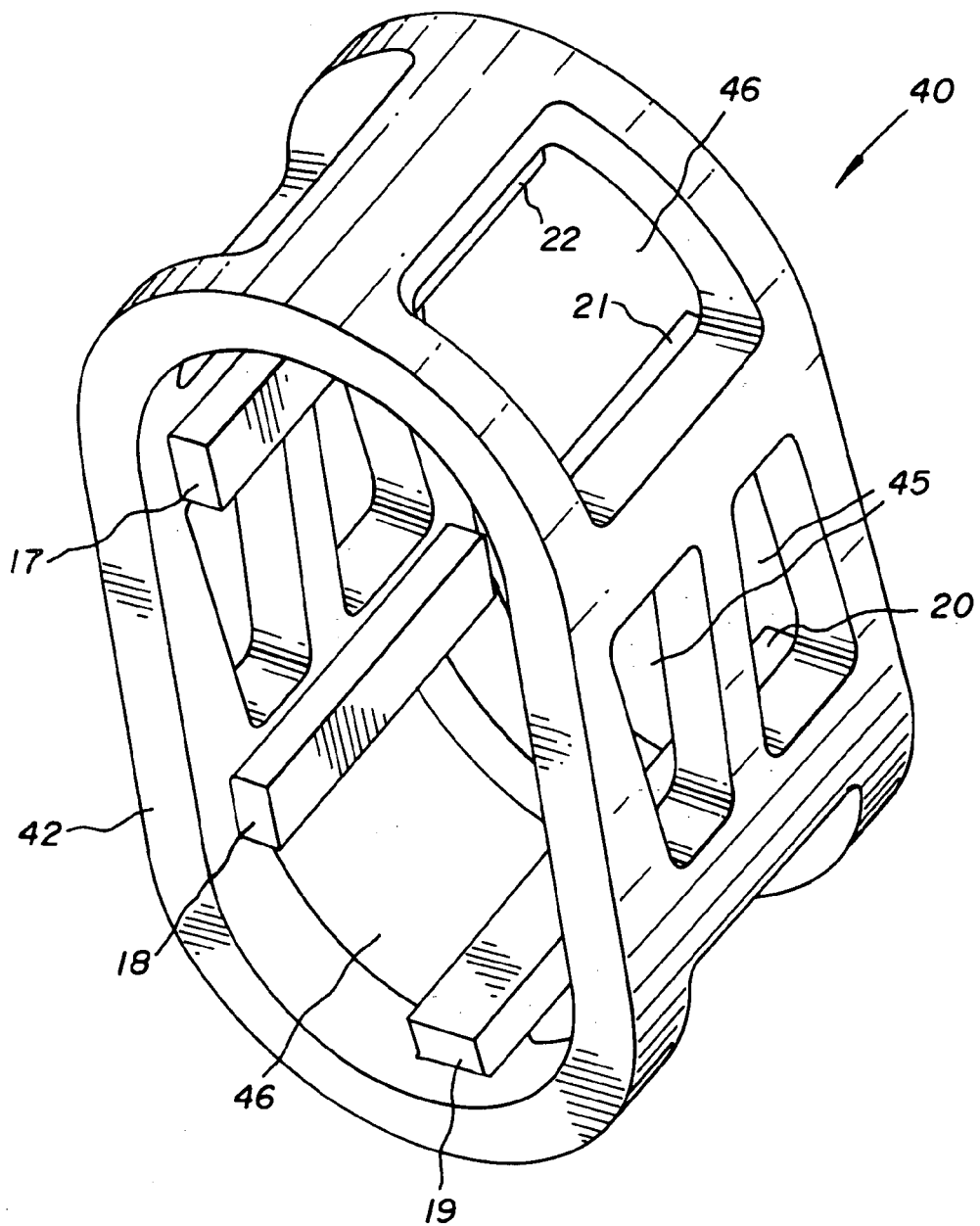
FIG. 13 is a bottom perspective view of the spacer tube of FIGS. 10–12.
Figure 14:
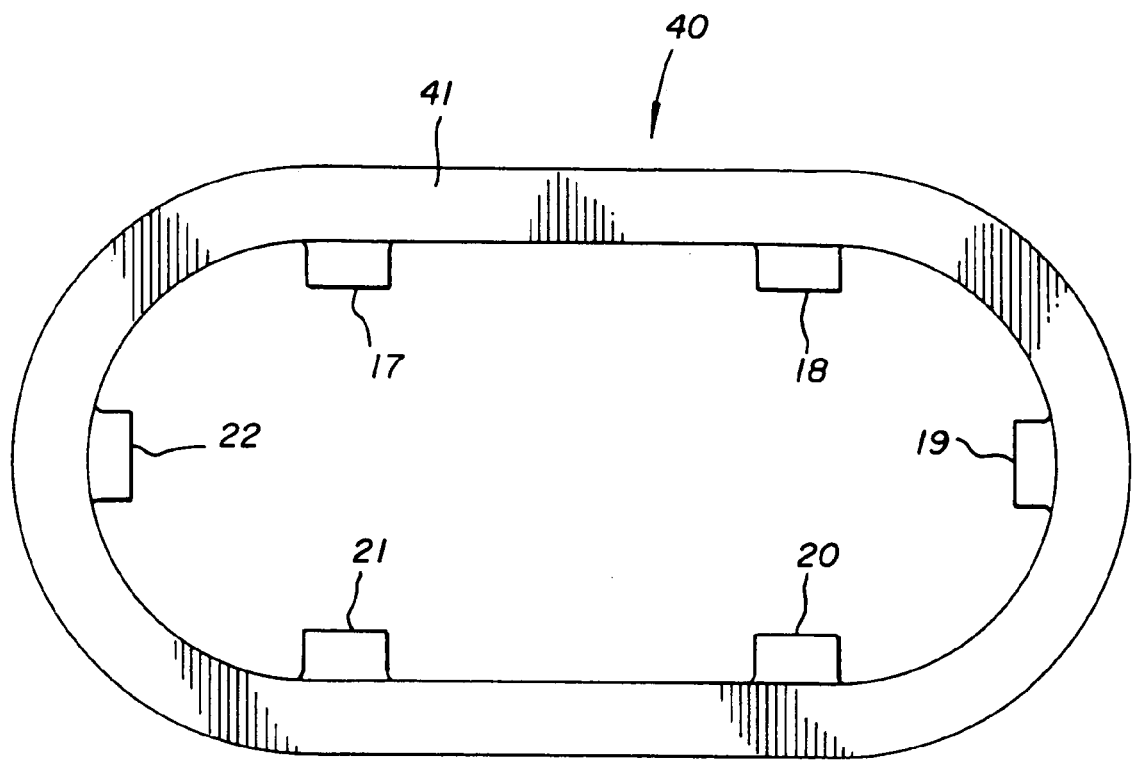
FIG. 14 is a top plan view of the spacer tube shown in FIGS. 10–13.
Figure 15:
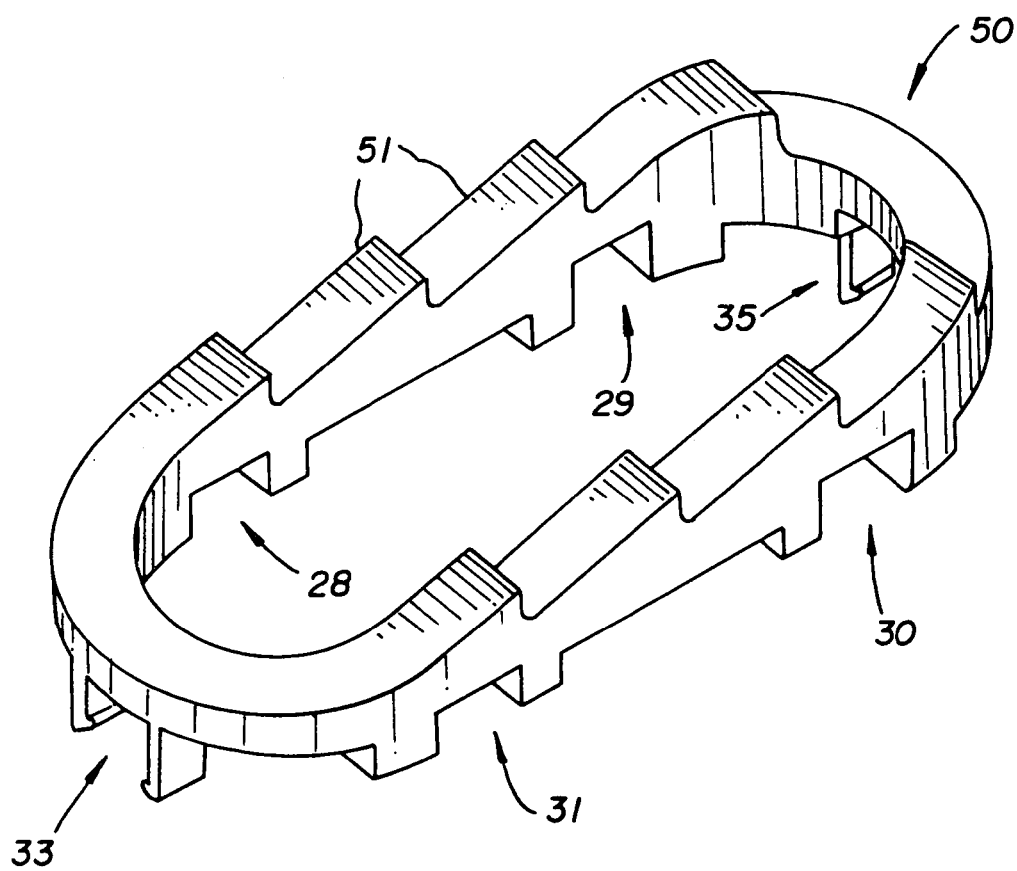
FIG. 15 is a top perspective view of the top end cap of FIGS. 10 and 11.

Referring to FIGS. 11–13, the oblong spacer assembly 38, and more particularly, the spacer tube 40, like the embodiment of FIGS. 1–9 has internal ribs 17–22 which correspond to the ribs 17–22 of FIGS. 1–9. The spacer tube 40 also has large openings on the side thereof including rectangular openings 46 and irregular trapezoid openings 45. However, owing to the shape of this particular embodiment, namely because of the rounded ends, larger rectangular openings 46 may be provided in this area than can be provided at 14a in the kidney shaped spacer assembly 10. Thus, an advantage of this particular embodiment is the larger openings to further enhance access for bone to grow and fuse with the spacer tube.

The oblong spacer tube assembly 38 can use a top end cap and a bottom end cap which have the smooth serrations 26 and 126 of the type shown in FIG. 8, but of course wherein the end cap itself would be oblong to fit into the oblong spacer tube 40. However, for purposes of illustration, FIGS. 10, 11 and 15–17 illustrate an alternate form of end cap. The top end cap 50 of FIGS. 10, 11 and 15–17 differs from the top end cap 25 of FIGS. 1–9 in two respects other than its being of oblong shape rather than kidney shape. First, it can be seen that the serrations 51 on the top of top end cap 50 are slanted to the right and terminate at sharp edges. The sharp edges provide a better gripping surface as between the serrations and the adjacent vertebral surface of the intervertebral space into which the spacer assembly is inserted. It is to be understood that the sharp serrations, while shown only in the embodiment of FIGS. 10–17, can be employed in any of the other embodiments.

Figure 16:
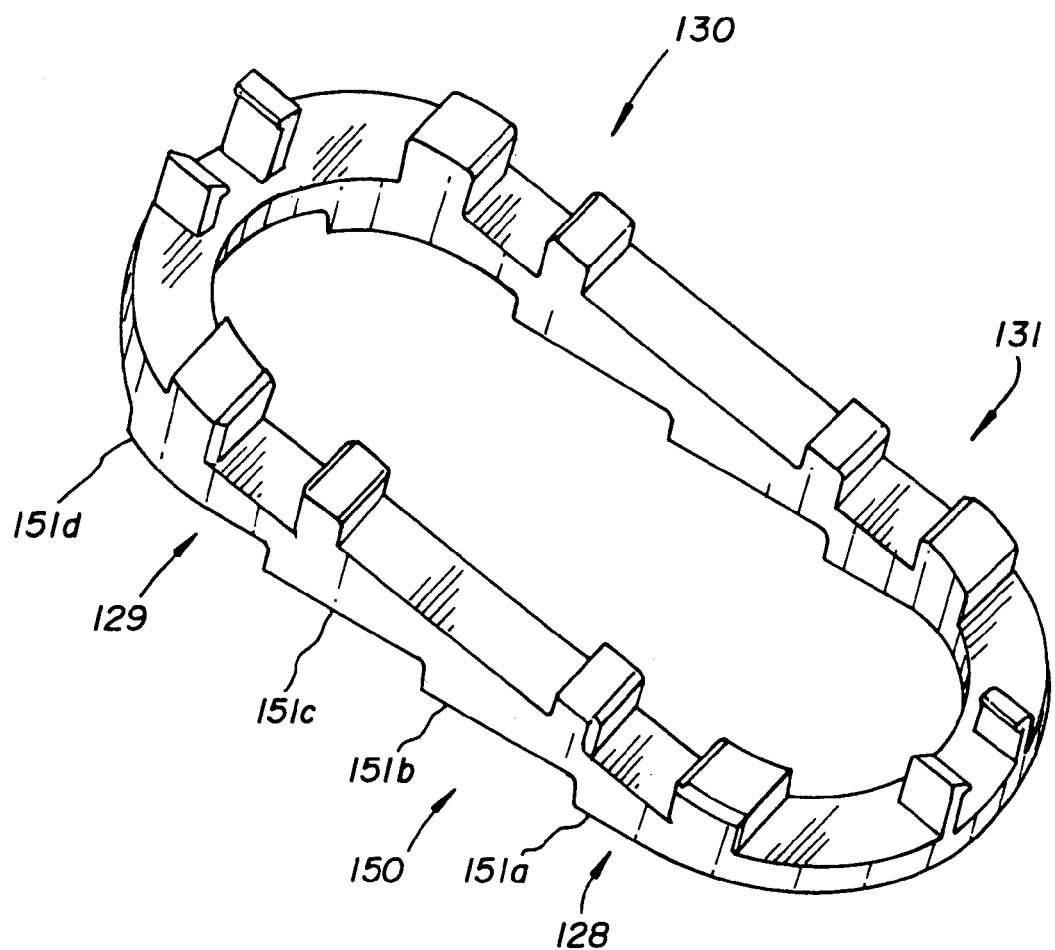
FIG. 16 is a top perspective view of the bottom end cap of FIGS. 10 and 11.
Figure 17:
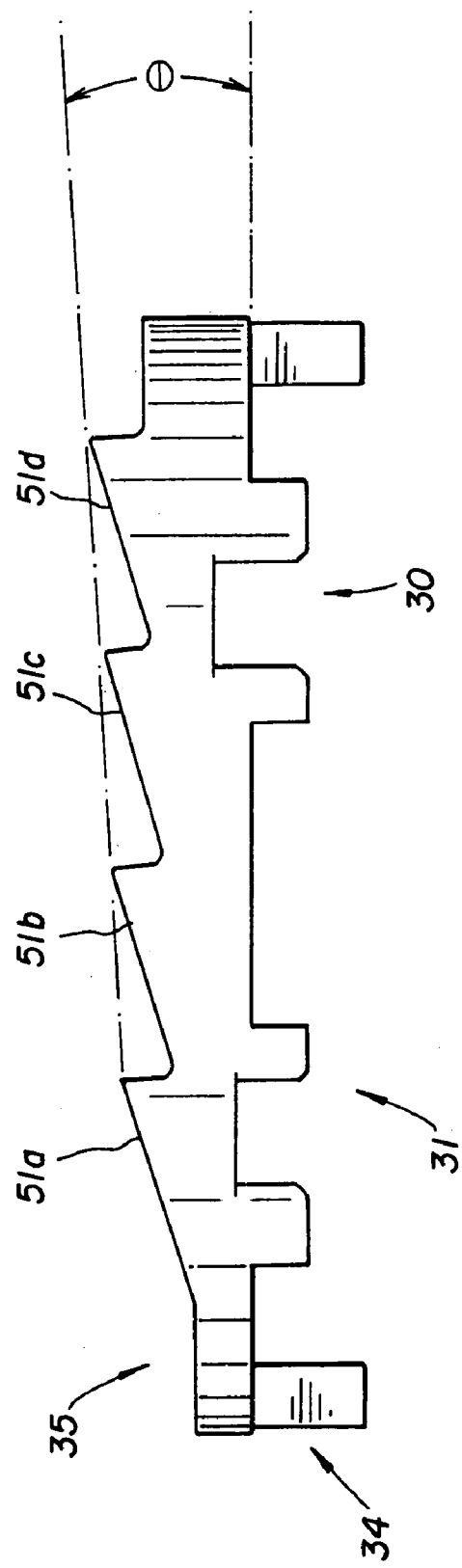
FIG. 17 is a side elevational view of an end cap for use with the spacer tube shown in FIGS. 10–13 but showing a modification.
Figure 18:
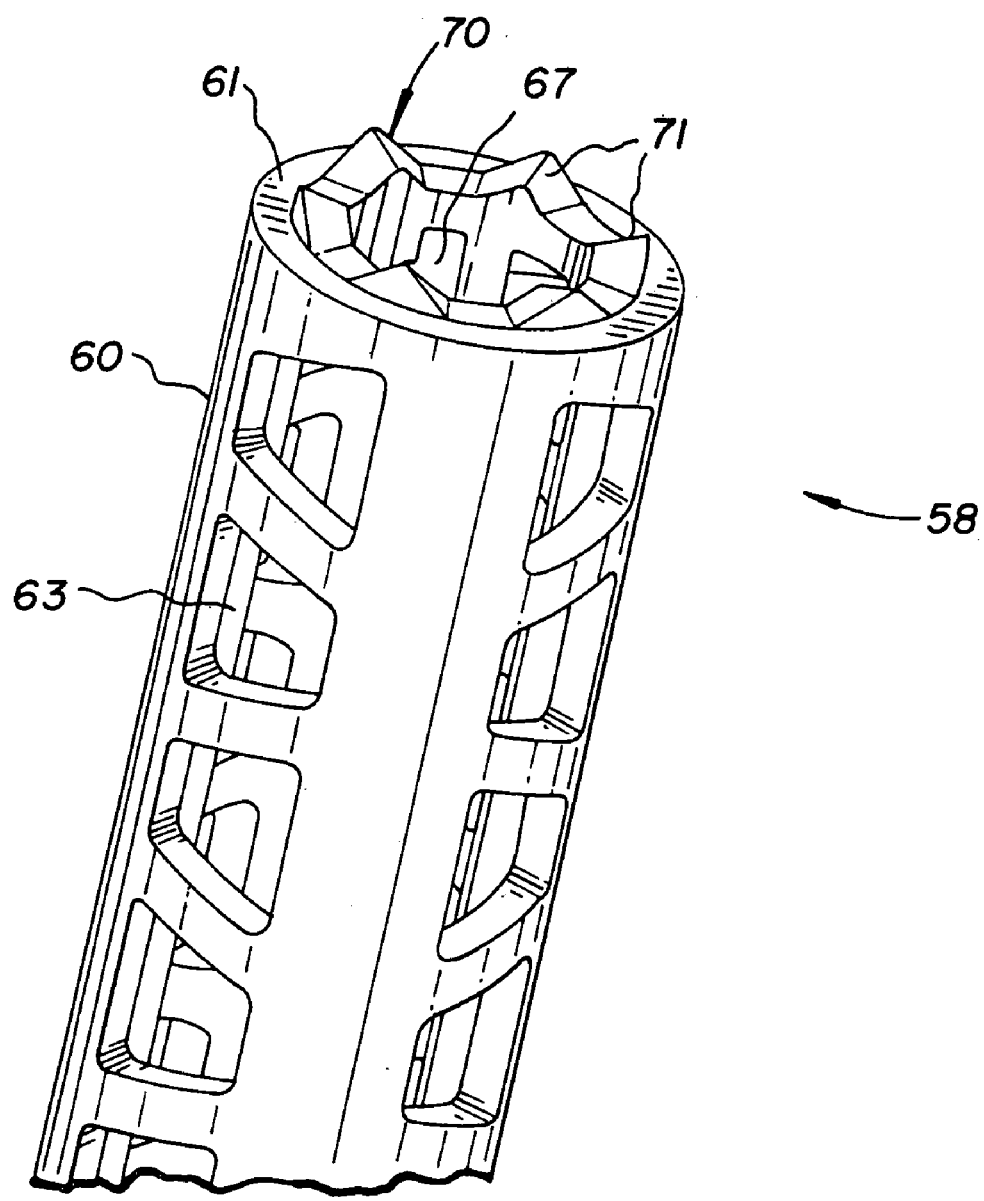
FIG. 18 is a top perspective view of a portion of another embodiment of a spinal spacer assembly which is circular.

Another improvement shown in the end cap 50 is that the individual serrations 51a, 51b, 51c and 51d are of an increasing height as is best seen in FIGS. 11 and 17. This permits use of the spacer assembly of the present invention to tilt the two vertebrae adjacent the intervertebral space by an angle θ where a lordosis angle is desired. A reverse inclination of the serrations 51a–51d can provide a kyphosis angle between the adjacent vertebrae. It is to be understood that the end caps with increasing heights, while shown only in the embodiment of FIGS. 10–17, can be employed in any of the other embodiments.

The bottom portion of the top end cap 50 is constructed and is mounted on the ribs 17–22 of the spacer assembly 38 in precisely the same manner as is the top end cap 25 of FIGS. 1–9. Accordingly, the mounting of the top end cap 50 onto the spacer tube 40 will not be explained in detail except by referring back to the discussion in the embodiment of FIGS. 1–9. Consistent therewith, the support posts of the top end cap 50 are generally designated by the same numerals 28, 29, 30 and 31; and the friction prongs are generally referred to by the same numerals 33 and 35. As explained above with respect to FIGS. 1–9, there is no limitation on the arrangement and number of support posts and friction prongs, provided that there is at least one of each.

The bottom end cap 150 shown in FIG. 16 is the mirror image of top end cap 50 and hence all numerals corresponding to similar parts are the same, raised by 100. Also shown therein are the four sharp serrations of differing heights, 151a–151d.

Although the top and bottom end caps of the embodiment of FIGS. 10–17 include serrations of differing heights, so as to create a lordosis or kyphosis angle, these serrations can also be of uniform height with sharp edges or with rounded crests such as serrations 26 and 126 of FIGS. 1–9.

The kidney shaped spacer assembly 10 of FIGS. 1–9 and the oblong shaped spacer assembly 38 of FIGS. 10–17 would be intended essentially for placement into an intervertebral space for fusion of the adjacent vertebrae. For this purpose, each of these spacer assemblies would be provided in different heights, for example, nine different heights from 7 to 15 mm. Even when the most appropriate height is chosen, a surgeon might want to trim the height of the selected spacer assembly just slightly at the site.

Figures 19, 20:
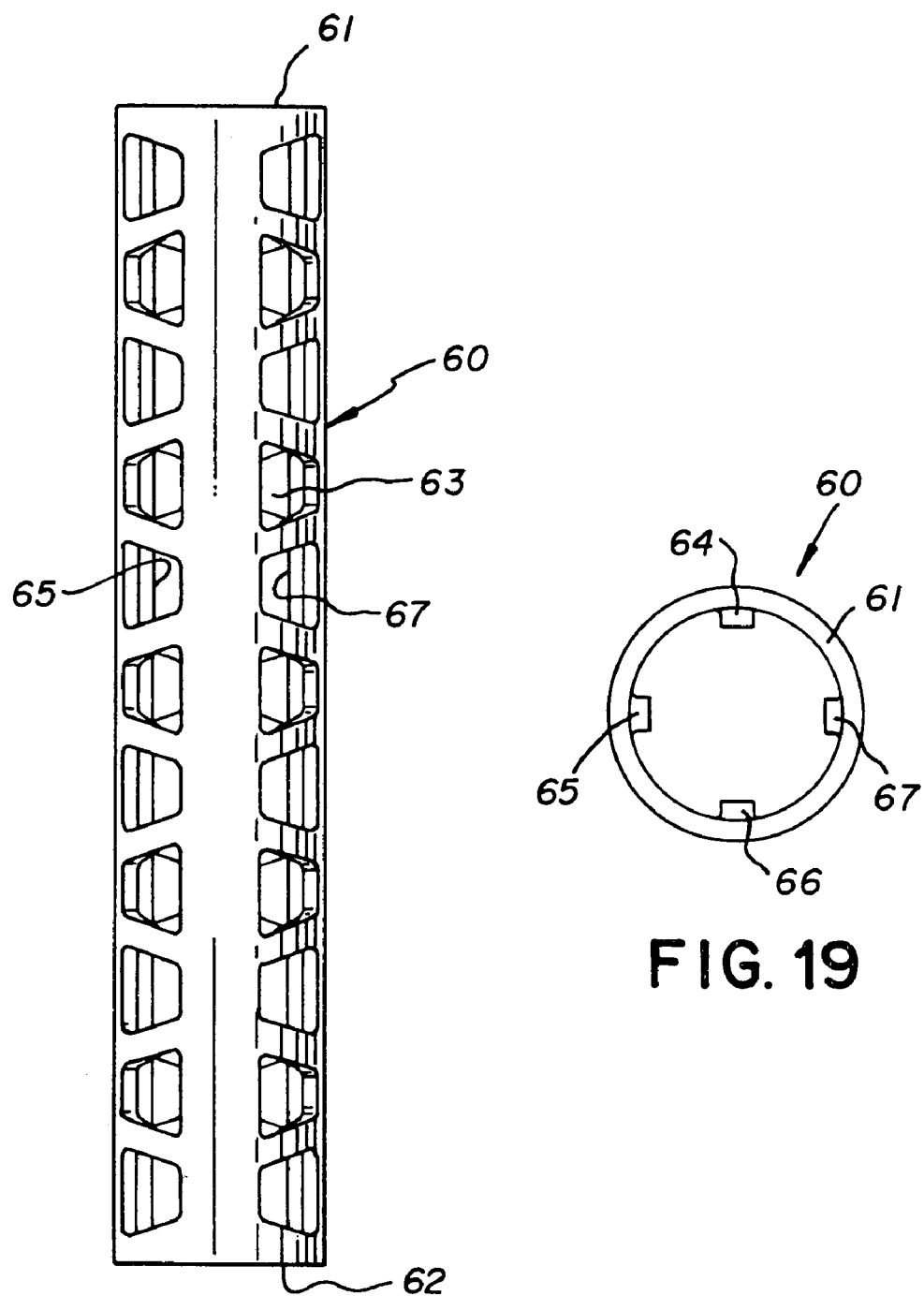
FIG. 19 is a side elevational view of the spacer tube of FIG. 18.
FIG. 20 is a top plan view of FIG. 19.

FIGS. 18–21 show another embodiment of the invention, namely a circular spacer assembly 58 which comprises a circular spacer tube 60 having a top surface 61 and a bottom surface 62. This spacer assembly 58 also has a plurality of ribs 64, 65, 66 and 67, as shown in FIG. 20 and a plurality of relatively large trapezoidal openings 63 in the side of spacer tube 60. It has been found that the regular isosceles trapezoidal openings 63 are particularly suitable for a circular spacer tube provided in long heights and which is to be cut to a shorter height.

Figure 21:
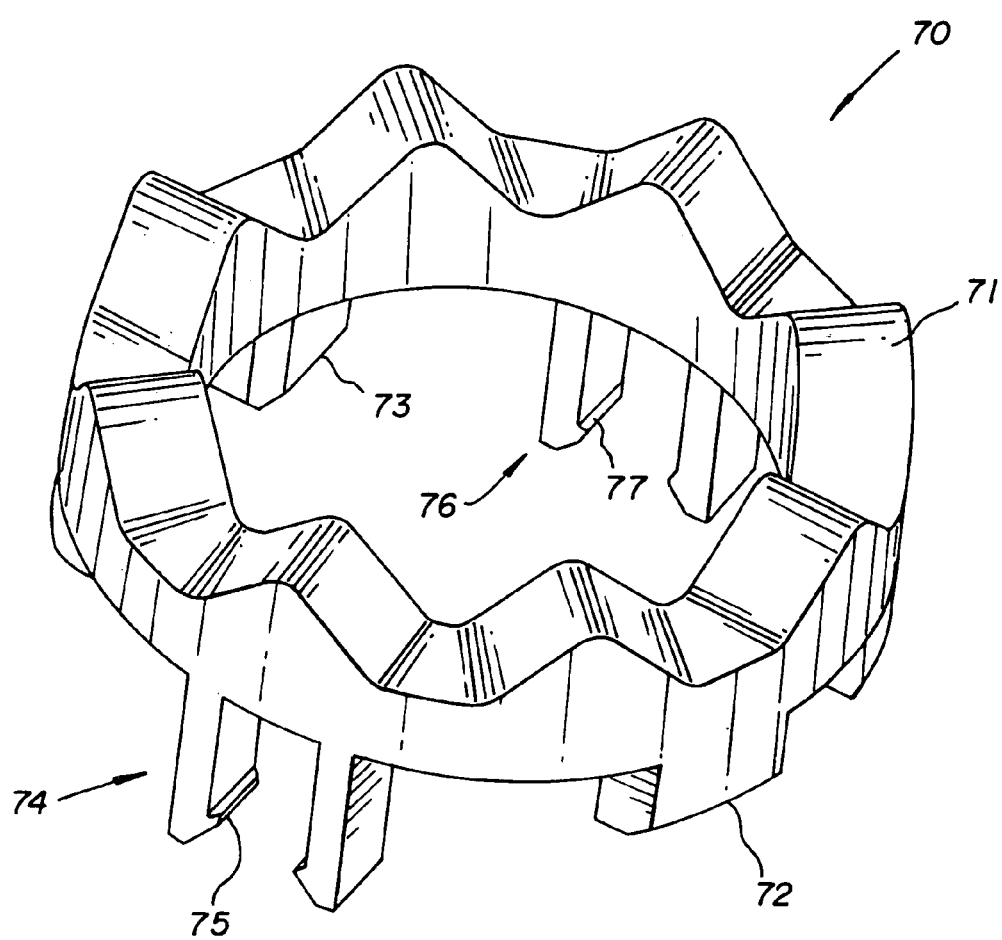
FIG. 21 is a top perspective view of the top end cap of FIG. 18.

FIG. 21 illustrates in perspective view a top end cap 70 for the spacer tube 60, the top end cap 70 comprising opposed support posts 72 and 73 and opposed friction prongs 74 and 76, each having, respectively, friction projections 75 and 77. The support posts 72 and 73 and the friction prongs 74 and 75 operate to engage selected ones of the ribs 64, 65, 66 and 67. For example, in this case the opposed support posts 72 and 73 would engage either the ribs 65 and 67 or the ribs 64 and 66 and in each case the friction prongs 74 and 76 would engage the other two opposed ribs.

It is to be understood that the top end cap 70 could have any one, two or three pairs of support posts with the remainder of the rib or ribs of the spacer tube receiving friction prongs. Top end cap 70 has a plurality of smooth serrations 71 which function similarly to the smooth serrations 26 in the embodiments of FIGS. 1–9. It is to be understood that a spacer tube assembly would also be provided with a bottom end cap which would be the mirror image of the top end cap 70.

It is noted that the round spacer tube 60 is relatively long compared with its width. For example, it can be provided in heights up to 130 mm. There are two reasons for this. First, this spacer tube can be cut transversely to form a spacer assembly of any height over a large range of heights. Second, the very long spacer tube 60 can be used in a corpectomy procedure wherein a portion of the vertebrae is cut out throughout its entire height, as are the discs above and below such vertebrae. A spacer tube 60 can then be cut to the desired length to extend along the entire length of the cutout vertebrae and extend across the intervertebral spaces located above and below that vertebrae to engage the vertebral surfaces of the two adjacent vertebrae.

Corpectomy can also be utilized for two or more adjacent vertebrae, wherein the spacer assembly would be placed in a cavity made in both of the adjacent vertebrae, the intervertebral discs therebetween and the two intervertebral discs above and below the two vertebrae.

Figure 22:
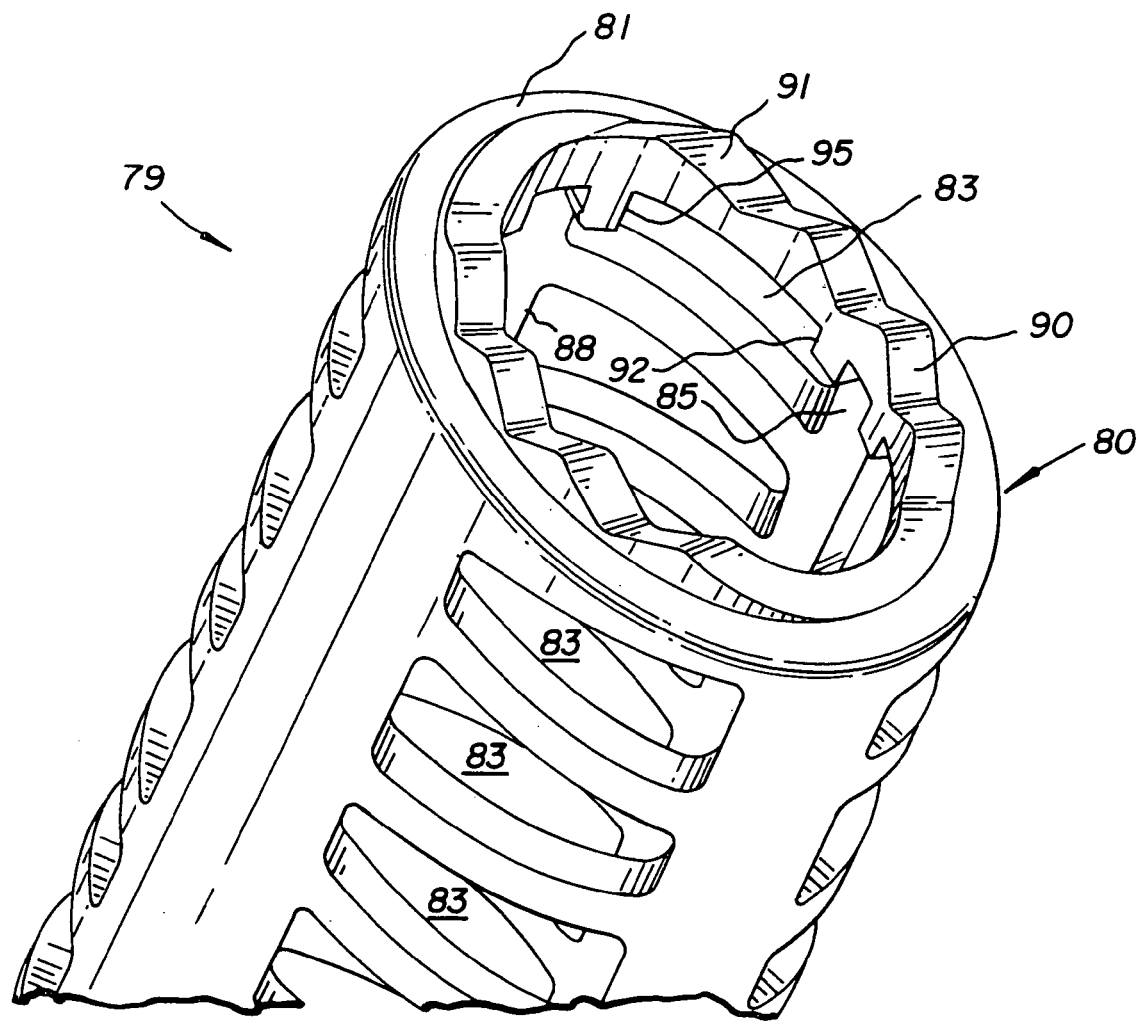
FIG. 22 is a top perspective view of another embodiment of a spinal spacer assembly which is oval.
Figure 23:
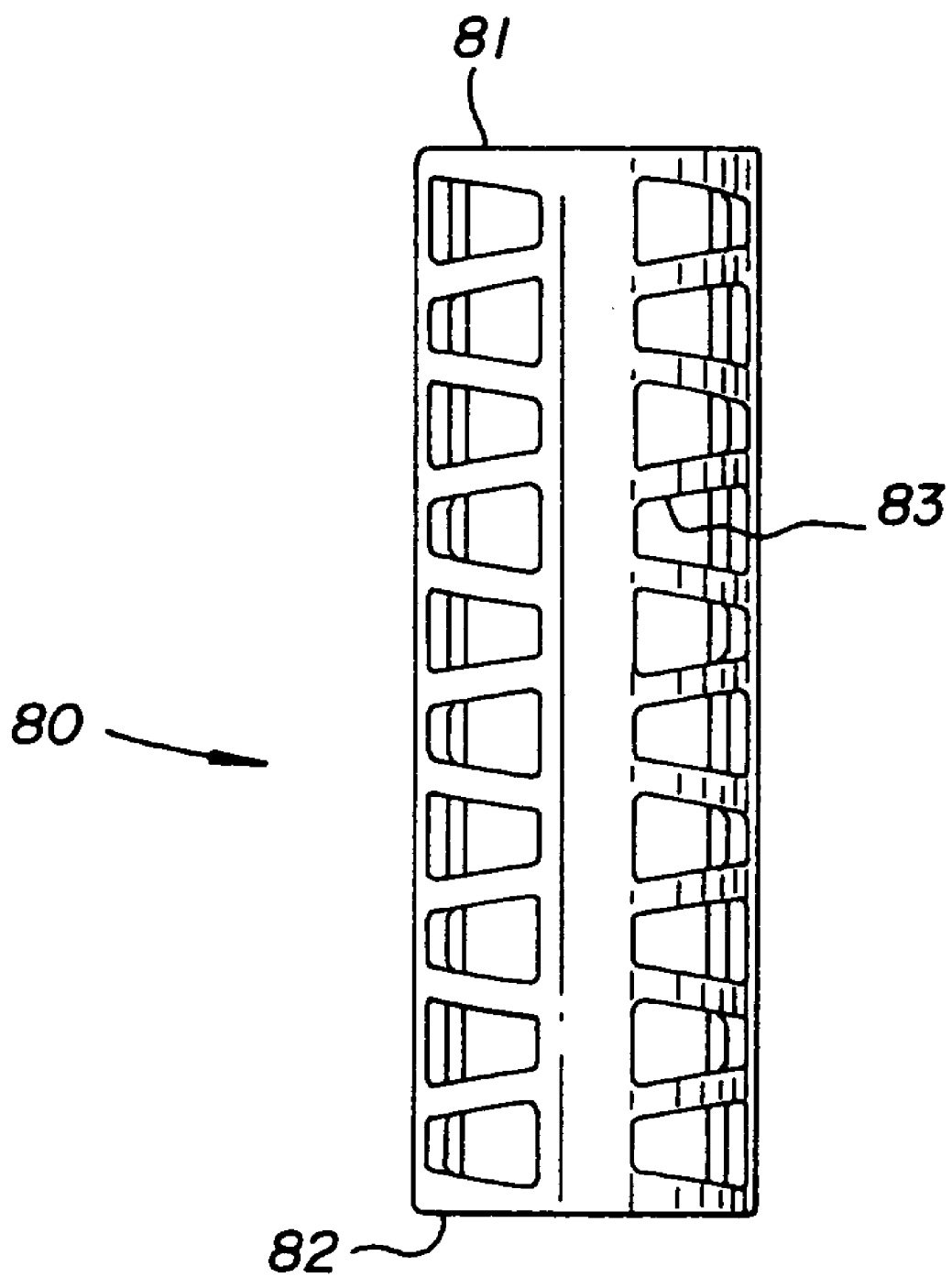
FIG. 23 is a side elevational view of the spacer tube of FIG. 22.
Figure 24:
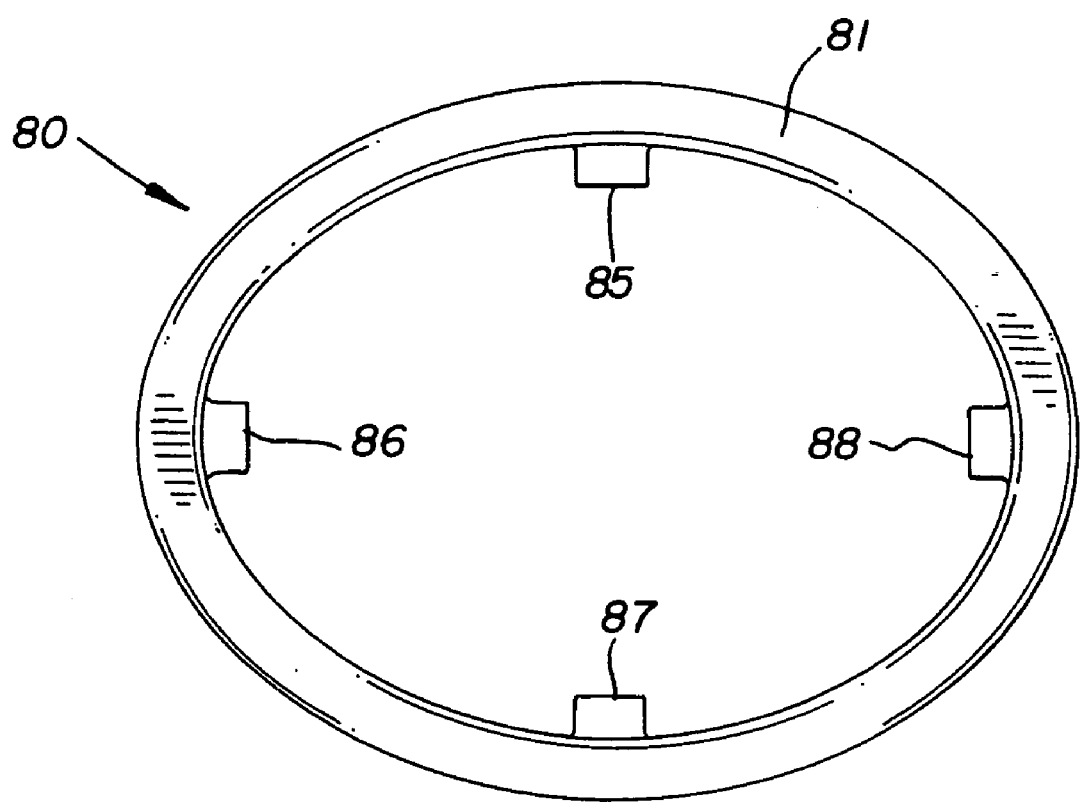
FIG. 24 is a top plan view of FIG. 23.
Figure 25:
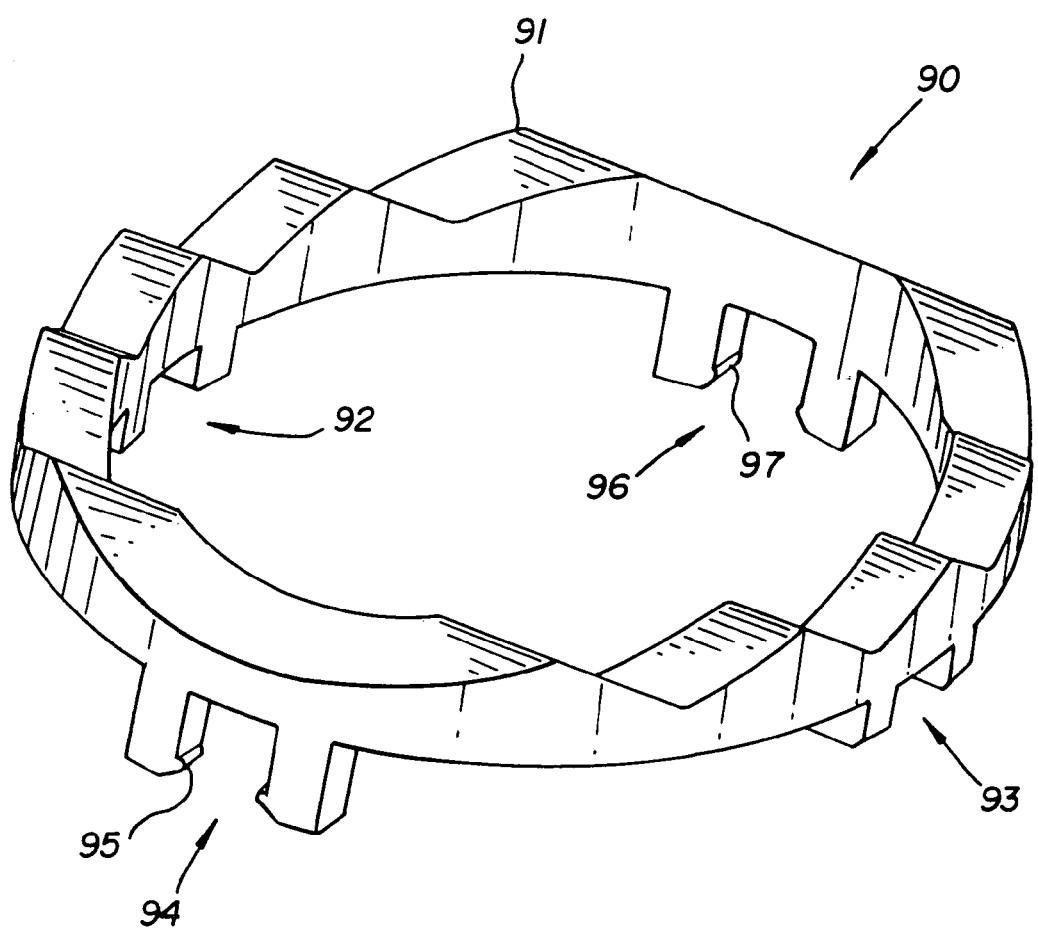
FIG. 25 is a top perspective view of the end cap for use with the spacer tube of FIGS. 22–24.

FIGS. 22–25 show an oval spacer assembly 79 and the components thereof, wherein FIG. 22 shows an oval spacer assembly, FIGS. 23 and 24 show the oval spacer tube 80 and FIG. 25 shows an upper end cap 90 therefor. The oval spacer assembly 79 is similar to the circular spacer assembly in its general construction and use. Specifically, like the circular spacer assembly, it can be provided in varying heights between 7 and 15 mm for intervertebral fusion or it can be provided in a very long height such as up to 130 mm for use in a corpectomy procedure either at its original height or after being trimmed back to a shorter height. The oval spacer tube 80 comprises a top 81 and a bottom 82 and side openings 83. As with the circular spacer assembly, the oval spacer assembly has regular trapezoidal openings through the side thereof. As with the circular spacer tube, these openings are suitable for a spacer tube which is a continuous curve and which in use could be cut to a shorter size. Spacer tube 80 further includes a plurality of ribs 85, 86, 87 and 88. These ribs, like the ribs in the circular spacer tube extend the complete height of the tube.

FIG. 25 shows an oval top end cap 90 for use with the spacer tube 80 to form a spacer assembly. This spacer tube 90 is provided with serrations 91 for the same reasons as discussed for the serrations in the earlier described embodiments. Also, the serration structure can be modified in all the different ways described above.

As with the earlier described embodiments, there can be any number of pairs of support posts, with the remainder of the ribs having friction prongs, or vice versa. In the illustrated embodiment, the top end cap 90 is provided with opposed pairs of support posts 92 and 93 which are positioned to engage the ribs 85 and 87 and a pair of friction prongs 94 and 96 having friction engaging projections 95 and 97, respectively, for engagement with the ribs 86 and 88. To complete the spacer assembly, the spacer tube 80 would also be provided with a bottom end cap which would be the mirror image of the top end cap shown in FIG. 25.

The spacer assemblies of the present invention are preferably made of surgical grade titanium alloy such as Ti-6Al-4V, ASTM F-1108.

In operation, one would select the desired shape of spacer assembly, initially the desired shape of spacer tube. A kidney shaped spacer assembly would generally be utilized only for posterior entry, offset to center, although it could be used for anterior entry. The oblong, circular and oval spacer assemblies could be applied both anteriorly and posteriorly. The circular and oval spacer tubes can be cut to a desired height for intervertebral fusion. Alternatively, the circular and oval spacer tubes can be cut to a very long height, possibly up to 130 mm for use in corpectomy.

After the desired shape of the spacer tube has been selected, appropriate end caps are selected, with serration properties as desired and as discussed above. The end caps are then press fit into the ends of the spacer tube to form the spacer assembly.

The dimensions of the various embodiments can be varied to suit different patient sizes and conditions. These typical dimensions are provided by way of example and not by way of limitation. The range of heights would preferably be between 7 mm and 15 mm, as discussed above. By way of example, typical other dimensions may be as follows. The circular spacer assembly may be provided with outside diameters of 10 mm, 12 mm, 14 mm and 16 mm. A rib in a circular spacer assembly can typically be 1 mm wide and extend 1 mm outwardly from the inside wall of the spacer tube. For the other shapes of spacer assemblies, the rib may typically have a width of approximately 1.8 mm and also extend 1 mm outwardly from the inside wall of the spacer tube. The kidney shaped spacer assembly could typically have an outside length and width (viewed from above) of 25 mm and 10 mm. The oblong spacer assembly could typically have an outside length and width (viewed from above) of 24 mm and 12 mm or 20 mm and 10 mm. The oval spacer assembly could typically have an outside length and width (viewed from above) of 22 mm and 17 mm, 28 mm and 22 mm, 33 mm and 27 mm and 26 mm and 22 mm.

Although the invention has been described in considerable detail with respect to preferred embodiments, it will be apparent that the invention is capable of numerous modifications and variations, apparent to those skilled in the art, without departing from the spirit and scope of the claims.

What is claimed is:

1. A spinal spacer tube assembly comprising:
   (a) a spacer tube that is open at each end, said tube comprising:
      (i) a side wall including a plurality of openings therethrough;
      (ii) a first longitudinal internal rib within the spacer tube, said rib including a pair of first rib sides and a pair of first rib ends;
      (iii) a second longitudinal internal rib within the spacer tube, said rib including a pair of second rib sides and a pair of second rib ends;
   (b) a pair of end caps, each of which comprises:
      (i) a pair of spaced support posts having a support surface therebetween, said pair of support posts being adapted to be placed over a first internal rib within the spacer tube so that the support posts are adjacent to the first rib sides and the support surface engages a first rib end in a load bearing relationship;

(ii) a pair of friction prongs that are adapted to engage the second rib sides of a second internal rib;

wherein at least one of the end caps includes a plurality of serrations that extend beyond the end of the spinal spacer tube when the end cap is installed thereon.

2. The assembly of claim 1 wherein at least one serration has a height that is different from the height of another serration.

* * * * *